Jan. 1, 1957 F. W. ANDERSON Plant Pat. 1,545

NECTARINE TREE

Filed Nov. 18, 1955

WITNESS

Addison F. Avery

INVENTOR

Frederic W. Anderson

Webster & Webster

ATTYS.

United States Patent Office

Plant Pat. 1,545
Patented Jan. 1, 1957

1,545

NECTARINE TREE

Frederic W. Anderson, Merced, Calif.

Application November 18, 1955, Serial No. 547,876
1 Claim. (Cl. 47—62)

This invention relates to a new and distinct variety of nectarine tree characterized by large size, yellow flesh, freestone fruit whose attractive exterior color is yellow partially over-spread with red.

As compared with the Sun Grand nectarine (United States Plant Patent No. 974), both are freestones, but the fruit of the present variety averages twenty percent larger; ripens about one week later; and—while having a somewhat shorter harvest season, less exterior color, and not quite as firm flesh—is of better eating quality.

The present variety of nectarine tree was originated by me at my experimental orchard located near Le Grand, California, during the course of a long and continuing program seeking improved varieties of fruit for commercial production, particularly peaches and nectarines.

The present variety is an F–1 cross of the Le Grand nectarine (United States Plant Patent No. 549) and the Sun Grand nectarine (United States Plant Patent No. 974); such cross having been accomplished by me under careful supervision and effective controls.

When the seedling tree resulting from such cross came into maturity it was recognized as being of especial value by reason of the distinctive characteristics herein enumerated, and I therefore selected such seedling tree for further propagation; asexual reproduction having been initially accomplished by top working—specifically by budding—on mature orchard trees in my experimental orchard located as aforesaid. Such asexual reproductions were found to carry forward all of the characteristics of the parent.

Figure 1:
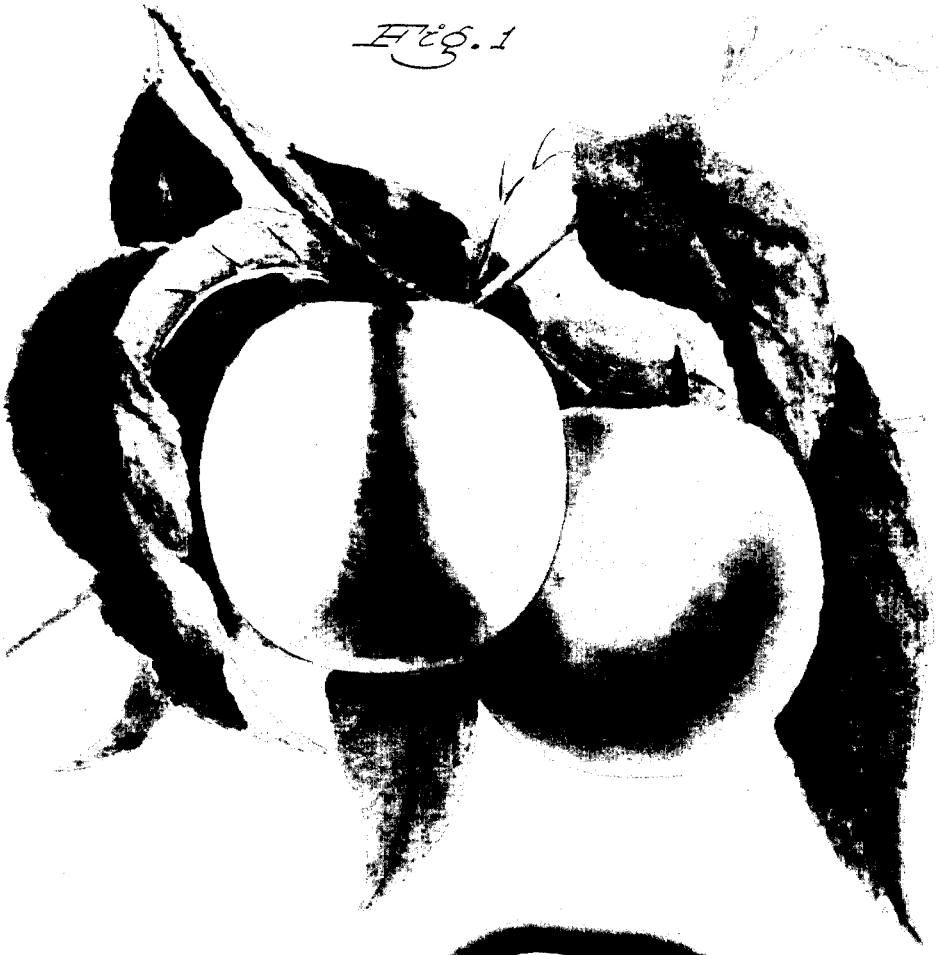
Fig. 1 is an elevation showing two of the fruit, together with twigs and leaves.
Figure 2:
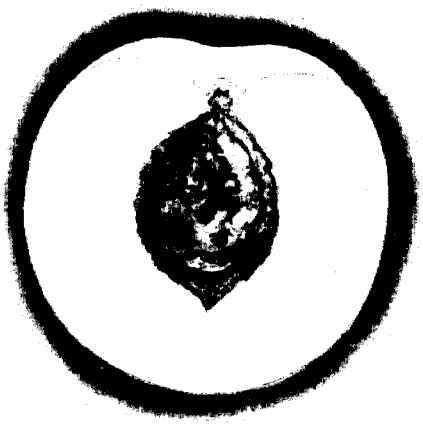
Fig. 2 is a sectional elevation of one of the fruit with the stone exposed.

Referring now more specifically to the pomological details of this new and distinct variety of nectarine tree, the following is an outline description thereof; all major color plate identifications being by reference to Maerz and Paul Dictionary of Color:

Tree:
- *Size.*—Large to medium.
- *Vigor.*—Vigorous.
- *Growth.*—Spreading.
- *Form.*—Vase formed.
- *Production.*—Productive.
- *Bearing.*—Regular bearer.

Trunk:
- *Size.*—Stocky.
- *Texture.*—Medium.

Branches:
- *Size.*—Stocky.
- *Texture.*—Smooth.
- *Color.*—Brown.

Leaves:
- *Size.*—Large to medium. Average length—6½"; average width—1½".
- *Margin.*—Crenate.
- *Petiole.*—Medium length; medium thickness.
- *Glands.*—Average number—four. Medium size; globose. Usually positioned two on petiole and two or more on blade.
- *Color.*—Top side—medium green (22–L–5). Under side—lighter green (21–J–6).

Flower buds:
- *Size.*—Medium.
- *Length.*—Medium.

Flowers:
- *First and full bloom.*—About with the July Elberta peach (United States Plant Patent No. 15).
- *Size.*—Large.

Fruit:
- *Maturity when described.*—Eating ripe.
- *Date of first picking.*—July 15, 1955.
- *Date of last picking.*—July 25, 1955.
- *Size.*—Uniform; large. Average diameter axially—2⅞". Average transversely in suture plane—2¾".
- *Form.*—Uniform; symmetrical; globose.
- *Suture.*—Shallow, with slight depression beyond pistil point.
- *Ventral surface.*—Rounded strongly; lips equal.
- *Cavity.*—Rounded. Average depth—½"; average breadth—⅝". Markings—red.
- *Base.*—Rounded.
- *Apex.*—Short; rounded.

Skin:
- *Thickness.*—Thick.
- *Texture.*—Tough.
- *Down.*—Wanting.
- *Color.*—Yellow (9–K–5 shading to 9–K–9), partially over-spread with red (3–L–11 shading to 6–L–6). In many fruit the red over-color follows and spreads from the suture, becoming very dark red (56–L–12) at the end of said suture adjacent the base.

Flesh:
- *Juice.*—Moderate; rich.
- *Texture.*—Firm; meaty.
- *Fibers.*—Few.
- *Ripens.*—Even.
- *Flavor.*—Sub-acid.
- *Aroma.*—Distinct.
- *Eating quality.*—Good to best.
- *Color.*—Yellow (9–L–4) shading darker (9–L–7) toward the skin, mottled with red (2–L–6) adjacent the stone.

Stone:
- *Type.*—Free. Parts from flesh smoothly.
- *Size.*—Large. Average length—1 13/16"; average breadth—1⅛"; average thickness—15/16".
- *Form.*—Obovoid.
- *Hilum.*—Oblong.
- *Sides.*—Equal.
- *Surfaces.*—Regularly furrowed near base. Pitted from base to above center.
- *Ridges.*—Rounded.
- *Pits.*—Elongated.
- *Ventral edge.*—Thick.
- *Dorsal edge.*—Full, with shallow groove.
- *Color.*—Brown (7–A–10), shading in part to reddish purple (7–E–6).

Use: Market; local; long distance shipping.
Shipping quality: Good.

The tree and its fruit herein described may vary in slight detail due to climatic and soil conditions under which the variety may be grown.

The following is claimed:

A new and distinct variety of nectarine tree, as illustrated and described, characterized by large size, yellow flesh, freestone fruit whose exterior color is yellow, partially over-spread with red; said fruit being further characterized—as compared with the freestone Sun Grand nectarine—by twenty percent larger size on the average, ripening about a week later, and—while having a shorter harvesting period, less exterior red color, and not quite as firm of flesh—being of better eating quality.

No references cited.